United States Patent [19]

Haga et al.

[11] Patent Number: 4,590,182

[45] Date of Patent: May 20, 1986

[54] ORGANOPHOSPHORUS COMPOUND AND INSECTICIDAL, MITICIDAL OR NEMATICIDAL COMPOSITION CONTAINING IT

[75] Inventors: Takahiro Haga, Kusatsu; Tadaaki Toki, Otsu; Toru Koyanagi, Kyoto; Hiroshi Okada, Kusatsu; Kiyomitsu Yoshida, Kusatsu; Osamu Imai, Kusatsu, all of Japan

[73] Assignee: Ishihara Sangyo Kaisha Ltd., Osaka, Japan

[21] Appl. No.: 668,938

[22] Filed: Nov. 7, 1984

[30] Foreign Application Priority Data

Nov. 11, 1983 [JP] Japan .................................. 58-212068
Dec. 23, 1983 [JP] Japan .................................. 58-243485
Aug. 28, 1984 [JP] Japan .................................. 59-179065
Sep. 7, 1984 [JP] Japan .................................. 59-187755
Sep. 11, 1984 [JP] Japan .................................. 59-190344

[51] Int. Cl.⁴ .......................... A01N 57/32; C07F 9/65
[52] U.S. Cl. .......................... 514/80; 514/92; 548/111
[58] Field of Search .................. 548/111; 514/80, 92

[56] References Cited

U.S. PATENT DOCUMENTS 2,843,586  7/1958  Melamed ............................... 544/88
3,661,926  5/1972  Van Den Bos et al. ............. 548/111

FOREIGN PATENT DOCUMENTS 144794   8/1984  Japan .
1024032  7/1966  United Kingdom .

256764   5/1970  U.S.S.R. .

OTHER PUBLICATIONS

Chemical Abstracts, vol. 73, No. 1, Jul. 6, 1970, p. 332, 3867f, Columbus Ohio, L. Levkova et al.; "Preparation of N-Phosphorylated 2-Oxo-1, 3-Oxazolidines and 6-Methyl-2-Oxo-1, 3-Tetrahydrooxazine".

*Primary Examiner*—Richard L. Raymond
*Attorney, Agent, or Firm*—Oblon, Fisher, Spivak, McClelland & Maier

[57] ABSTRACT

An organophosphorus compound represented by the general formula:

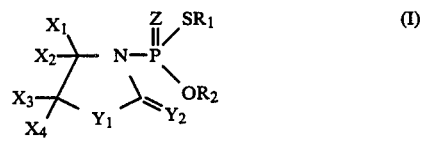

where each of $X_1$ and $X_3$ is a hydrogen atom; an alkyl or alkoxy group which may be substituted by halogen, alkoxy, alkylthio, phenoxy, halogenated phenoxy, phenylthio or halogenated phenylthio; a carboxyl group; an alkoxycarbonyl group; or a phenyl group which may be substituted by halogen, each of $X_2$ and $X_4$ is a hydrogen atom or an alkyl group, provided that $X_2$ and $X_3$ may together form an alkylene group, each of $Y_1$, $Y_2$ and $Z$ is an oxygen atom or a sulfur atom, and each of $R_1$ and $R_2$ is an alkyl group.

13 Claims, No Drawings

ORGANOPHOSPHORUS COMPOUND AND INSECTICIDAL, MITICIDAL OR NEMATICIDAL COMPOSITION CONTAINING IT

The present invention relates to novel organophosphorus compounds having insecticidal, miticidal and nematicidal activities. More particularly, the present invention relates to organophosphorus compounds containing a substituted 2-oxazolidinone (or substituted 2-oxazolidinethione) ring or a substituted 2-thiazolidinone (or substituted 2-thiazolidinethione) ring, a process for preparing such organophosphorus compounds, and an insecticidal, miticidal or nematicidal composition containing such a phosphorus compound as an active ingredient.

The organophosphorus compounds containing a substituted 2-oxazolidinone (or substituted 2-oxazolidinethione) ring or a substituted 2-thiazolidinone (or substituted 2-thiazolidinethione) ring of the present invention are novel compounds. Japanese Unexamined Patent Publication No. 144794/1984 discloses organophosphorus compounds containing a 1,3-oxa(or thia)zolidine-2-thione ring. However, the disclosed compounds are different in their chemical structure from the compounds of the present invention, and they are used as an activating agent for a carboxyl group. There is no disclosure which indicates or suggests the use of the present invention, i.e. the use as an insecticidal, miticidal or nematicidal compound.

Namely, the present invention provides novel organophosphorus compounds represented by the following general formula I, which include stereo isomers such as optical isomers:

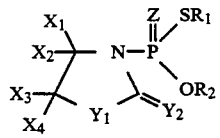

where each of $X_1$ and $X_3$ is a hydrogen atom; an alkyl or alkoxy group which may be substituted by halogen, alkoxy, alkylthio, phenoxy, halogenated phenoxy, phenylthio or halogenated phenylthio; a carboxyl group; an alkoxycarbonyl group; or a phenyl group which may be substituted by halogen, each of $X_2$ and $X_4$ is a hydrogen atom or an alkyl group, provided that $X_2$ and $X_3$ may together form an alkylene group, each of $Y_1$, $Y_2$ and $Z$ is an oxygen atom or a sulfur atom, and each of $R_1$ and $R_2$ is an alkyl group.

The present invention also provides a process for preparing the compounds of the formula I, which comprises reacting a compound represented by the general formula:

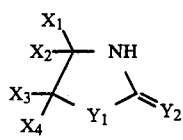

where $X_1$, $X_2$, $X_3$, $X_4$, $Y_1$ and $Y_2$ are as defined above, with a compound represented by the general formula:

where Hal is a halogen atom and Z, $R_1$ and $R_2$ are as defined above, in the presence of an acid-acceptor.

Further, the present invention provides an insecticidally, miticidally or nematicidally effective amount of an organophosphorus compound of the formula I.

Now, the present invention will be described in detail with reference to the preferred embodiments.

In the above-mentioned general formula I, the alkyl group or the alkyl moiety of the alkoxy group represented by $X_1$ to $X_4$, or the alkyl group represented by $R_1$ and $R_2$, includes methyl, ethyl, propyl or butyl. As halogen in the halogenated alkyl, alkoxy, phenoxy, phenylthio or phenyl group represented by $X_1$ and $X_3$, there may be mentioned fluorine, chlorine, bromine or iodine.

In the above formula I, each of $X_1$ and $X_3$ is preferably a hydrogen atom; a lower alkyl ($C_{1-6}$) or lower alkoxy ($C_{1-6}$) group which may be substituted by alkoxy or alkylthio; or a phenyl group which may be substituted by halogen, more preferably a hydrogen atom; a lower alkyl group which may be substituted by alkoxy or alkylthio; or a lower alkoxy group, most preferably a hydrogen atom or a lower alkyl group.

Each of $X_2$ and $X_4$ is preferably a hydrogen atom or a lower alkyl ($C_{1-6}$) group.

Each of $Y_2$ and Z is preferably an oxygen atom.

Each of $R_1$ and $R_2$ is preferably a lower alkyl ($C_{1-6}$) group. More preferably $R_1$ and $R_2$ are defferent from each other, most preferably $R_1$ is a n-propyl group, an iso-butyl group or a sec-butyl group, and $R_2$ is a methyl group or an ethyl group.

As mentioned above, the compounds of the formula I of the present invention may be prepared by a process represented by the following formulas:

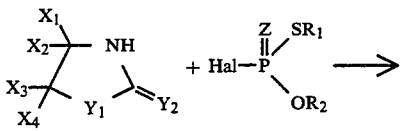

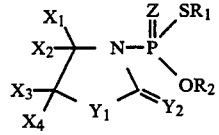

where Hal is a halogen atom, and $X_1$, $X_2$, $X_3$, $X_4$, $Y_1$, $Y_2$, Z, $R_1$ and $R_2$ are as defined above.

This reaction is usually conducted within a temperature range of from $-100°$ to $50°$ C., preferably from $-80°$ C. to room temperature ($30°$ C.).

This reaction is conducted in the presence of an acid-acceptor. As the acid-acceptor, there may be mentioned an organic lithium compound such as n-butyl lithium, tert-butyl lithium or phenyl lithium; an inorganic base such as sodium hydroxide, potassium hydroxide, sodium hydride or potassium hydride; or an organic base such as triethylamine or pyridine. Further, the reaction is preferably conducted in a solvent. As the solvent, there may be mentioned an aromatic hydrocarbon such as benzene, toluene, xylene or chlorobenzene; a cyclic or non-cyclic aliphatic hydrocarbon such as hexane or cyclohexane; an ether such as diethyl ether, methyl ethyl ether, dioxane or tetrahydrofuran; a nitrile such as acetonitrile, propionitrile or acrylonitrile; or an aprotic polar solvent such as dimethylformamide, dimethylsulfoxide, sulfolane or hexamethylphosphoric triamide.

Among the starting materials represented by the general formula II, a substituted 2-oxazolidinone (or substituted 2-oxazolidinethione) can be readily prepared by a ring-forming reaction of a substituted β-amino alcohol with urea, phosgene or a dialkyl carbonate (or thiophosgene), and a substituted 2-thiazolidinethione can be readily obtained by a ring-forming reaction of a sulfuric acid ester of a substituted β-amino alcohol with carbon disulfide. Further, a substituted 2-thiazolidinone may also be readily prepared by (1) a ring-forming reaction of a substituted β-aminomercaptan with urea, (2) an oxidation reaction of a substituted 2-thiazolidinethione, or (3) a ring-forming reaction of a sulfuric acid ester of a substituted β-amino alcohol with carbonyl sulfide.

Now, the present invention will be described in further detail with reference to Examples. However, it should be understood that the present invention is by no means restricted by these specific Examples.

EXAMPLE 1

Preparation of trans O-ethyl S-n-propyl [4-(4-chlorophenyl)-5-methyl-2-oxo-3-thiazolidinyl]-phosphonothiolate (Compound No. 2)

(1) 9.3 g of erythro-1-amino-1-(4-chlorophenyl)-2-propyl sulfuric acid ester was suspended in 60 ml of ethanol, and 40 ml of an aqueous solution containing 5.4 g of carbon disulfide and 4.4 g of potassium hydroxide was gradually dropwise added thereto. The mixture was reacted at 40° C. for 3 hours under stirring. After the completion of the reaction, ethanol was distilled off under reduced pressure, and the residue was extracted with ethyl acetate. The extracted layer was washed with water and dried over anhydrous sodium sulfate, and the solvent was distilled off under reduced pressure, whereby 5.0 g of trans-4-(4-chlorophenyl)-5-methyl-2-thiazolidinethione was obtained.

(2) 5.0 g of trans-4-(4-chlorophenyl)-5-methyl-2-thiazolidinethione obtained by the above reaction (1) was dissolved in 50 ml of methanol, and 30 ml of a methanol solution containing 5.35 g of sodium methoxide was added thereto. Then, 10.7 g of a 30% hydrogen peroxide aqueous solution was gradually dropwise added thereto at a temperature of not higher than 40° C., and the mixture was reacted at room temperature for 1 hour under stirring. After the completion of the reaction, methanol was distilled off under reduced pressure, and the residue was extracted with ethyl acetate. The extracted layer was washed with water and dried over anhydrous sodium sulfate, and the solvent was distilled off under reduced pressure, whereby 1.8 g of trans-4-(4-chlorophenyl)-5-methyl-2-thiazolidinone having a melting point of from 119° to 121° C. was obtained.

(3) 0.8 g of trans-4-(4-chlorophenyl)-5-methyl-2-thiazolidinone obtained by the above reaction (2) was dissolved in 20 ml of tetrahydrofuran, and the solution was cooled to −78° C. Then, 2.3 ml of a n-hexane solution of n-butyl lithium (1.65M) was gradually dropwise added thereto, and the mixture was stirred for 30 minutes. Then, 5 ml of a tetrahydrofuran solution containing 0.78 g of O-ethyl S-n-propyl phosphorochloridothiolate was gradually dropwise added thereto, and the mixture was stirred for 30 minutes, and then reacted at room temperature for 3 hours. After the completion of the reaction, the reaction product was poured into ice water, and extracted with ethyl acetate. The extracted layer was washed with water and dried over anhydrous sodium sulfate. Then, the solvent was distilled off under reduced pressure, and the residue was purified by silica gel column chromatography, whereby 0.5 g of the desired product having a refractive index of 1.5426 (at 24.6° C.) was obtained.

EXAMPLE 2

Preparation of trans O-ethyl S-n-propyl [5-(4-chlorophenyl)-4-methyl-2-oxo-3-thiazolidinyl]-phosphonothiolate (Compound No. 1)

1.0 g of trans-5-(4-chlorophenyl)-4-methyl-2-thiazolidinone prepared in the same manner as the reactions (1) and (2) of Example 1, was dissolved in 20 ml of tetrahydrofuran, and the solution was cooled to −78° C. Then, 3.2 ml of a n-hexane solution of n-butyl lithium (1.65M) was gradually dropwise added thereto, and the mixture was stirred for 30 minutes. Then, 5 ml of a tetrahydrofuran solution containing 1.0 g of O-ethyl S-n-propyl phosphorochloridothiolate was gradually dropwise added thereto. The mixture was stirred for 30 minutes, and then reacted at room temperature for 3 hours. After the completion of the reaction, the reaction product was poured into ice water, and extracted with ethyl acetate. The extracted layer was washed with water and dried over anhydrous sodium sulfate. Then, the solvent was distilled off under reduced pressure, and the residue was purified by silica gel column chromatography, whereby 1.0 g of the desired product having a refractive index of 1.5592 (at 27.6° C.) was obtained.

EXAMPLE 3

Preparation of S-sec-butyl O-ethyl (2-oxo-3-thiazolidinyl)phosphonothiolate (Compound No. 5) 1.5 g of 2-thiazolidinone prepared in the same manner as the reactions (1) and (2) of Example 1, was dissolved in 30 ml of tetrahydrofuran, and the solution was cooled to −78° C. Then, 11 ml of a n-hexane solution of n-butyl lithium (1.65M) was gradually dropwise added thereto, and the mixture was stirred for 15 minutes. Then, 10 ml of a tetrahydro- furan solution containing 5 g of S-sec-butyl O-ethyl phosphorochloridothiolate was gradually dropwise added thereto. The mixture was stirred for 30 minutes, and then reacted at room temperature for 3 hours. After the completion of the reaction, the reaction product was poured into water and extracted with ethyl acetate. The extracted layer was washed with water and dried over anhydrous sodium sulfate. Then, the solvent was distilled off under reduced pressure, whereby 2.3 g of the desired product having a refractive index of 1.5334 (at 19.6° C.) was obtained.

EXAMPLE 4

Preparation of S-sec-butyl O-ethyl (5-methyl-2-oxo-3-oxazolidinyl)phosphonothiolate (Compound No. 9)

(1) A mixture comprising 10 g of 1-amino-2-propanol, 20 ml of diethyl carbonate and 67 mg of sodium methoxide, was reacted for 15 hours under reflux. After the completion of the reaction, about 14 ml of ethanol was distilled under normal pressure, and the residue was distilled off under reduced pressure, whereby 7.6 g of 5-methyl-2-oxazolidinone having a boiling point of from 150 to 155° C./7 mmHg was obtained.

(2) 2.0 g of 5-methyl-2-oxazolidinone was dissolved in 40 ml of tetrahydrofuran, and the solution was cooled to −78° C. Then, 12 ml of a n-hexane solution of n-butyl lithium (1.65M) was gradually dropwise added thereto, and the mixture was stirred for 15 minutes. Then, 10 ml of a tetrahydrofuran solution containing 4.3 g of S-sec-butyl O-ethyl phosphorochloridothiolate was gradually dropwise added, and the mixture was stirred for 30 minutes and then reacted at room temperature for 2 hours. After the completion of the reaction, the reaction product was poured into water, and extracted with ethyl acetate. The extracted layer was washed with water and dried over anhydrous sodium sulfate. Then, the solvent was distilled off under reduced pressure, and the residue was purified by silica gel column chromatography, whereby 1.6 g of the desired product having a refractive index of 1.4923 (at 20.5° C.) was obtained.

EXAMPLE 5

Preparation of O-ethyl S-n-propyl (4-ethyl-2-oxo-3-oxazolidinyl)phosphonothiolate (Compound No. 20, etc.)

2.5 g of 4-ethyl-2-oxazolidinone prepared in the same manner as the reaction (1) of Example 4, was dissolved in 40 ml of tetrahydrofuran, and the solution was cooled to −78° C. Then, 14 ml of a n-hexane solution of n-butyl lithium (1.55M) was gradually dropwise added thereto, and the mixture was stirred for 10 minutes. Then, 5.3 g of O-ethyl S-n-propyl phosphorochloridothiolate was gradually dropwise added thereto, and the mixture was returned to room temperature and reacted for 2.5 hours. After the completion of the reaction, the solvent was distilled off, and the residue was poured into water and extracted with ethyl acetate. The extracted layer was washed with a saturated sodium chloride aqueous solution and dried over anhydrous sodium sulfate. Then, the solvent was distilled off under reduced pressure, and the residue was purified by silica gel column chromatography, whereby 3.84 g of the desired product (Compound No. 20) having a refractive index of 1.4948 (at 22.6° C.) was obtained.

This compound has diastereomers as it contains an asymmetric carbon atom at the 4-position of the oxazolidine ring and an asymmetric phosphorus atom. The above compound was subjected to diastereomeric resolution by silica gel column chromatography, whereby Compound No. 20a having a refractive index of 1.4956 (at 19.8° C.) and Compound No. 20b having a refractive index of 1.4950 (at 20.3° C.) were isolated.

Separately, the preparation and isolation were conducted in the same manner as in the above Example except that (+)-4-ethyl-2-oxazolidinone ($[\alpha]_D^{30}+4.29°$ (C 1.86, CHCl$_3$)) prepared by using L-2-amino-1-butanol instead of 4-ethyl-2-oxazolidinone used in Example 5, was used as the starting material, whereby Compound No. 20a-I having a refractive index of 1.4982 (at 16.2° C.) (one component of Compound No. 20a, $[\alpha]_D^{30}-46.19°$ (C4.55, CHCl$_3$)) and Compound No. 20b-I having a refractive index of 1.4978 (at 16.2° C.) (one component of Compound No. 20b, $[\alpha]_D^{30}-2.12°$ (C 20.28, CHCl$_3$)) were obtained.

Likewise, the preparation and isolation were conducted in the same manner by using (−)-4-ethyl-2-oxazolidinone ($[\alpha]_D^{30}-2.48°$ (C 2.82, CHCl$_3$)) prepared by using D-2-amino-1-butanol, as the starting material, whereby Compound No. 20a-II having a refractive index of 1.4990 (at 14.8° C.) (the other component of Compound No. 20a, $[\alpha]_D^{30}+62.33°$ (C 9.45, CHCl$_3$)) and Compound No. 20b-II having a refractive index of 1.4966 (at 17.2° C.) (the other component of Compound No. 20b, $[\alpha]_D^{30}+4.53°$ (C 11.70, CHCl$_3$)) were obtained.

EXAMPLE 6

Preparation of S-sec-butyl O-ethyl (4,4-dimethyl-2-oxo-3-oxazolidinyl)phosphonothiolate (Compound No. 39)

1.0 g of 4,4-dimethyl-2-oxazolidinone prepared in the same manner as the reaction (1) of Example 4, was dissolved in 10 ml of tetrahydrofuran, and the solution was cooled to −78° C. Then, 5.3 ml of a n-hexane solution of n-butyl lithium (1.65M) was gradually dropwise added thereto, and the mixture was stirred for 15 minutes. Then, 1.88 g of S-sec-butyl O-ethyl phosphorochloridothiolate was gradually dropwise added thereto, and the mixture was stirred for 30 minutes and then reacted at room temperature for 3 hours. After the completion of the reaction, the reaction product was poured into water, and extracted with ethyl acetate. The extracted layer was washed with water and dried over anhydrous sodium sulfate, and then the solvent was distilled off under reduced pressure. The residue was purified by silica gel column chromatography, whereby 1.1 g of the desired product having a refractive index of 1.4899 (at 19.2° C.) was obtained.

EXAMPLE 7

Preparation of S-sec-butyl O-ethyl (5,5-dimethyl-2-oxo-3-oxazolidinyl)phosphonothiolate (Compound No. 41)

1.5 g of 5,5-dimethyl-2-oxazolidinone prepared in the same manner as the reaction (1) of Example 4, was dissolved in 30 ml of tetrahydrofuran, and the solution was cooled to −78° C. Then, 10 ml of a n-hexane solution of n-butyl lithium (1.65M) was gradually dropwise added thereto, and the mixture was stirred for 15 minutes. Then, 10 ml of a tetrahydrofuran solution containing 3.1 g of S-sec-butyl O-ethyl phosphorochloridothiolate, was gradually dropwise added, and the mixture was stirred for 30 minutes and then reacted at room temperature for 3 hours. After the completion of the reaction, the product was poured into water and extracted with ethyl acetate. The extracted layer was washed with water and dried over anhydrous sodium sulfate, and the solvent was distilled off under reduced pressure. The residue was purified by silica gel chromatography, whereby 1.7 g of the desired product having a refractive index of 1.4877 (at 16.0° C.) was obtained.

EXAMPLE 8

Preparation of S-sec-butyl O-ethyl (4-methoxy-2-oxo-3-oxazolidinyl)phosphonothiolate (Compound No. 55)

1.2 g of 4-methoxy-2-oxazolidinone was dissolved in 30 ml of tetrahydrofuran, and the solution was cooled to −78° C. Then, 7.5 ml of a n-hexane solution of n-butyl lithium (1.65M) was gradually dropwise added thereto, and the mixture was stirred for 15 minutes. Then, 10 ml of a tetrahydrofuran solution containing 2.4 g of S-sec-butyl O-ethyl phosphorochloridothiolate was gradually dropwise added thereto. And the mixture was stirred for 30 minutes and then reacted at room temperature for 3 hours. After the completion of the reaction, the reaction product was poured into ice water, and extracted with ethyl acetate. The extracted layer was washed with water and dried over anhydrous sodium sulfate, and the solvent was distilled off under reduced pressure. The crude product thereby obtained was purified by silica gel column chromatography, whereby 0.6 g of the desired product having a refractive index of 1.4955 (at 14.6° C.) was obtained.

EXAMPLE 9

Preparation of S-sec-butyl O-ethyl (4-methoxy-5-trichloromethyl-2-oxo-3-oxazolidinyl)-phosphonothiolate (Compound No. 54)

2.3 g of 4-methoxy-5-trichloromethyl-2-oxazolidinone was dissolved in 30 ml of tetrahydrofuran, and the solution was cooled to −78° C. Then, 6.5 ml of a n-hexane solution of n-butyl lithium (1.65M) was gradually dropwise added, and the mixture was stirred for 15 minutes, then, 10 ml of a tetrahydrofuran solution containing 2.5 g of S-sec-butyl O-ethyl phosphorochloridothiolate was gradually dropwise added thereto, and the mixture was stirred for 30 minutes and then reacted at room temperature for 3 hours. After the completion of the reaction, the reaction product was poured into ice water and extracted with ethyl acetate. The extracted layer was washed with water and dried over anhydrous sodium sulfate, and then the solvent was distilled off under reduced pressure. The crude product thereby obtained was purified by silica gel column chromatography, whereby 0.9 g of the desired product having a refractive index of 1.5052 (at 17.4° C.) was obtained.

EXAMPLE 10

Preparation of S-sec-butyl O-ethyl (5-trifluoromethyl-2-oxo-3-oxazolidinyl)phosphonothiolate) (Compound No. 56a, b)

(1) A mixture comprising 4.0 g of 5-trichloromethyl-2-oxazolidinone and 20 ml of antimony pentafluoride, was reacted at 150° C. for 4.5 hours under stirring. After the completion of the reaction, the reaction mixture was poured into water, and extracted with methylene chloride. The extracted layer was washed with a saturated sodium chloride aqueous solution and then dried over anhydrous sodium sulfate. Methylene chloride was distilled off, and the residue was purified by silica gel column chromatography, whereby 1.2 g of 5-trifluoromethyl-2-oxazolidinone having a melting point of from 61° to 65° C. was obtained.

(2) 0.50 g of 5-trifluoromethyl-2-oxazolidinone was dissolved in 10 ml of tetrahydrofuran, and the solution was cooled to −78° C. Then, 2.10 ml of a n-hexane solution of n-butyl lithium (1.55M) was gradually dropwise added, the mixture was stirred for 15 minutes. Then, 2 ml of a tetrahydrofuran solution containing 0.77 g of S-sec-butyl O-ethyl phosphorochloridothiolate was gradually dropwise added thereto, and then the mixture was returned to room temperature and stirred for 14 hours. After the completion of the reaction, the reaction product was poured into water, and extracted with ethyl acetate. The extracted layer was washed with water and dried over anhydrous sodium sulfate, and the solvent was distilled off under reduced pressure. The residue was purified and separated by silica gel column chromatography whereby 0.24 g of the desired product having a refractive index of 1.4538 (at 24.4° C.) (Compound No. 56a) and 0.32 g of the other desired product as a diastereomer thereof having a refractive index of 1.4500 (at 24.2° C.) (Compound No. 56b) were obtained.

EXAMPLE 11

Preparation of methyl 3-[sec-butylthio(ethoxy)phosphinyl]-2-oxazolidinone-4-carboxylate (Compound No. 58)

1.5 g of methyl 2-oxazolidinone-4-carboxylate was dissolved in 30 ml of tetrahydrofuran, and the solution was cooled to −78° C. Then, 6.9 ml of a n-hexane solution of n-butyl lithium (1.65M) was gradually dropwise added thereto. The mixture was stirred for 15 minutes at the same temperature, and then 5 ml of a tetrahydrofuran solution containing 2.7 g of S-sec-butyl O-ethyl phosphorochloridothiolate was gradually dropwise added thereto. After the completion of the dropwise addition, the mixture was gradually returned to room temperature and reacted for 2 hours. After the completion of the reaction, the reaction mixture was poured into 100 ml of ice water, and then extracted with ethyl acetate. The extracted layer was dried over anhydrous sodium sulfate, and then the solvent was distilled off. The crude product thereby obtained was purified by silica gel column chromatography, whereby 1.7 g of the desired product having a refractive index of 1.4950 (at 16.1° C.) was obtained.

EXAMPLE 12

Preparation of S-sec-butyl O-ethyl (4-methylthiomethyl-2-oxo-3-oxazolidinyl)phosphonothiolate (Compound No. 66a, b)

1.5 g of 4-methylthiomethyl-2-oxazolidinone was dissolved in 30 ml of tetrahydrofuran, and the solution was cooled to −78° C. Then, 8.0 ml of a n-hexane solution of n-butyl lithium (1.55M) was gradually dropwise added thereto. The mixture was stirred for 15 minutes under the same temperature, and then 5 ml of a tetrahydrofuran solution containing 2.4 g of S-sec-butyl O-ethyl phosphorochloridothiolate was gradually dropwise added thereto. After the dropwise addition, the mixture was gradually returned to room temperature and reacted for 2 hours. After the completion of the reaction, the reaction mixture was poured into 100 ml of ice water, and extracted with ethyl acetate. The extracted layer was dried over anhydrous sodium sulfate, and then the solvent was distilled off. The crude product thereby obtained was purified and separated by silica gel chromatography, whereby 0.6 g of the desired product having a refractive index of 1.5068 (Compound No. 66a) and 0.58 g of the other desired product as a diastereomer having a refractive index of 1.5102 (at 27.4° C.) (Compound No. 66b) were obtained.

Representative specific compounds of the present invention prepared in Examples 1 to 12 or by a common process are presented in Table 1.

TABLE 1

$$\begin{array}{c} X_1 \\ X_2 \\ X_3 \\ X_4 \end{array} \diagdown N - \underset{Y_1 \diagup \diagdown Y_2}{\overset{Z \diagup SR_1}{\underset{\|}{P}}} \diagdown OR_2 \quad (I)$$

| Compound No. | X₁ | X₂ | X₃ | X₄ | Y₁ | Y₂ | Z | R₁ | R₂ | Physical property (Refractive index) |
|---|---|---|---|---|---|---|---|---|---|---|
| 1 | CH₃ | H | –C₆H₄–Cl | H | S | O | O | C₃H₇(n) | C₂H₅ | $n_D^{27.6}$ 1.5592 |
| 2 | –C₆H₄–Cl | " | CH₃ | " | " | " | " | " | " | $n_D^{24.6}$ 1.5426 |
| 3 | CH₃ | " | –C₆H₅ | " | " | " | " | C₄H₉(s) | " | $n_D^{17.8}$ 1.5550 |
| 4 | H | " | H | " | O | " | " | " | " | $n_D^{19.6}$ 1.5003 |
| 5 | " | " | " | " | S | " | " | " | " | $n_D^{19.6}$ 1.5334 |
| 6 | " | " | " | " | " | S | " | " | " | $n_D^{20.3}$ 1.5704 |
| 7a | CH₃ | " | " | " | O | O | " | " | " | $n_D^{16.6}$ 1.4925 |
| 7b | " | " | " | " | " | " | " | " | " | $n_D^{16.4}$ 1.4942 |
| 8a | C₂H₅ | " | " | " | " | " | " | " | " | $n_D^{18.2}$ 1.4941 |
| 8b | " | " | " | " | " | " | " | " | " | $n_D^{18.2}$ 1.4925 |
| 9 | H | " | CH₃ | " | " | " | " | " | " | $n_D^{20.5}$ 1.4923 |
| 10 | " | " | " | " | S | " | " | C₃H₇(n) | " | $n_D^{19.2}$ 1.5195 |
| 11 | " | " | " | " | " | S | " | C₄H₉(s) | " | $n_D^{18.9}$ 1.5680 |
| 12 | CH₃ | " | " | " | " | O | " | C₃H₇(n) | " | $n_D^{15.6}$ 1.5210 |
| 13 | " | " | " | " | " | S | " | " | " | $n_D^{19.2}$ 1.5640 |
| 14 | H | " | –C₆H₅ | " | " | " | " | C₄H₉(s) | " | $n_D^{18.2}$ 1.6053 |
| 15 | " | " | " | " | " | O | " | C₃H₇(n) | " | $n_D^{19.2}$ 1.5552 |
| 16 | " | " | –(CH₂)₄– | " | " | S | " | " | " | $n_D^{15.4}$ 1.5676 |
| 17 | CH₃ | H | –C₆H₅ | " | O | O | " | " | " | $n_D^{15.8}$ 1.5375 |
| 18 | H | " | C₂H₅ | " | " | " | " | C₄H₉(s) | " | $n_D^{16.6}$ 1.4915 |
| 19 | " | " | CH₃ | " | " | " | " | CH₃ | CH₃ | $n_D^{19.5}$ 1.5060 |
| 20 | C₂H₅ | " | H | " | " | " | " | C₃H₇(n) | C₂H₅ | $n_D^{22.6}$ 1.4948 |
| 20a | " | " | " | " | " | " | " | " | " | $n_D^{19.8}$ 1.4956 |
| 20b | " | " | " | " | " | " | " | " | " | $n_D^{20.3}$ 1.4950 |
| 20a-I | " | " | " | " | " | " | " | " | " | $n_D^{16.2}$ 1.4982 |
| 20b-I | " | " | " | " | " | " | " | " | " | $n_D^{16.2}$ 1.4978 |
| 20a-II | " | " | " | " | " | " | " | " | " | $n_D^{14.8}$ 1.4990 |

TABLE 1-continued $$\underset{X_4}{\overset{X_1}{\underset{X_3}{\bigg|}}}\underset{Y_1}{\overset{X_2}{\bigg|}}\text{C}-\text{N}-\overset{Z}{\underset{\parallel}{P}}\overset{SR_1}{\underset{OR_2}{\diagdown}}$$ (I)

| | General formula I | | | | | | | | | Physical property |
|---|---|---|---|---|---|---|---|---|---|---|
| Compound No. | $X_1$ | $X_2$ | $X_3$ | $X_4$ | $Y_1$ | $Y_2$ | $Z$ | $R_1$ | $R_2$ | (Refractive index) |
| 20b-II | " | " | " | " | " | " | " | " | " | $n_D^{17.2}$ 1.4966 |
| 21 | CH₃ | " | CH₃ | " | S | " | " | —C₄H₉(s) | " | $n_D^{16.2}$ 1.5185 |
| 22a | H | " | C₂H₅ | " | " | " | " | " | " | $n_D^{16.6}$ 1.4912 |
| 22b | " | " | " | " | " | " | " | " | " | $n_D^{16.6}$ 1.4966 |
| 23 | " | " | " | " | O | " | " | C₃H₇(n) | " | $n_D^{16.8}$ 1.4951 |
| 24 | " | " | C₄H₉(t) | " | " | " | " | " | " | $n_D^{16.4}$ 1.4900 |
| 25 | CH₃ | " | CH₃ | " | " | " | " | —C₄H₉(s) | " | $n_D^{16.6}$ 1.4902 |
| 26 | H | " | C₄H₉(t) | " | " | " | " | " | " | $n_D^{16.8}$ 1.4892 |
| 27a | C₃H₇(i) | " | H | " | " | " | " | " | " | $n_D^{18.4}$ 1.4920 |
| 27b | " | " | " | " | " | " | " | " | " | $n_D^{18.4}$ 1.4920 |
| 28 | H | " | " | " | " | S | " | " | " | $n_D^{18.8}$ 1.5489 |
| 29 | " | " | " | " | S | O | " | C₃H₇(n) | " | $n_D^{25.6}$ 1.5304 |
| 30 | C₂H₅ | " | " | " | O | " | " | —C₄H₉(s) | CH₃ | $n_D^{27.4}$ 1.4929 |
| 31 | H | " | CH₃ | " | S | " | " | " | C₂H₅ | $n_D^{27.0}$ 1.5168 |
| 32 | CH₃ | " | H | " | " | " | " | " | " | $n_D^{26.4}$ 1.5175 |
| 33 | C₂H₅ | " | " | " | " | " | " | " | " | $n_D^{25.2}$ 1.5170 |
| 34 | H | " | C₃H₇(i) | " | O | " | " | " | " | $n_D^{27.2}$ 1.4833 |
| 35 | " | " | H | " | S | " | " | " | CH₃ | $n_D^{27.6}$ 1.5414 |
| 36 | C₂H₅ | " | " | " | O | " | " | —C₄H₉(i) | C₂H₅ | $n_D^{28.0}$ 1.4827 |
| 37 | H | " | " | " | S | " | " | " | " | $n_D^{28.0}$ 1.5204 |
| 38 | " | " | " | " | O | " | " | " | " | $n_D^{28.0}$ 1.4902 |
| 39 | CH₃ | CH₃ | " | " | " | " | " | C₄H₉(s) | " | $n_D^{19.2}$ 1.4899 |
| 40 | H | H | " | C₂H₅ | " | " | " | " | " | $n_D^{14.8}$ 1.4908 |
| 41 | " | " | " | CH₃ | " | " | " | " | " | $n_D^{16.0}$ 1.4877 |
| 42 | CH₃ | CH₃ | H | H | " | " | " | C₄H₉(i) | " | $n_D^{28.0}$ 1.4814 |
| 43 | " | " | " | " | S | O | " | C₄H₉(s) | " | $n_D^{30.4}$ 1.5083 |
| 44 | " | " | " | " | O | S | " | " | " | $n_D^{28.2}$ 1.5279 |
| 45 | H | H | CH₃ | CH₃ | " | O | " | C₃H₇(n) | " | $n_D^{28.4}$ 1.4820 |
| 46 | CH₃ | CH₃ | H | H | " | " | " | C₄H₉(s) | CH₃ | $n_D^{28.4}$ 1.4890 |
| 47 | " | " | " | " | S | " | " | C₃H₇(n) | C₂H₅ | $n_D^{30.4}$ 1.5181 |
| 48 | " | " | " | " | " | S | " | C₄H₉(s) | " | $n_D^{28.8}$ 1.5669 |
| 49 | " | " | " | " | O | O | " | C₃H₇(n) | " | $n_D^{27.0}$ 1.4868 |
| 50 | H | H | CCl₃ | " | S | " | " | C₄H₉(s) | " | $n_D^{16.0}$ 1.5124 |
| 51 | " | " | " | " | O | " | " | " | " | $n_D^{17.2}$ 1.5202 |
| 52 | " | " | CH₂Cl | " | " | " | " | " | " | $n_D^{16.7}$ 1.5033 |
| 53 | " | " | CH₂Br | " | " | " | " | C₃H₇(n) | " | $n_D^{21.2}$ 1.5076 |
| 54 | CH₃O | " | CCl₃ | " | " | " | " | C₄H₉(s) | " | $n_D^{17.4}$ 1.5052 |
| 55 | " | " | H | " | " | " | " | " | " | $n_D^{14.6}$ 1.4955 |
| 56a | H | " | CF₃ | " | " | " | " | " | " | $n_D^{24.4}$ 1.4538 |
| 56b | " | " | " | " | " | " | " | " | " | $n_D^{24.2}$ 1.4500 |
| 57 | " | " | " | " | " | " | " | " | CH₃ | $n_D^{29.0}$ 1.4478 |
| 58 | COOCH₃ | " | H | " | " | " | " | " | C₂H₅ | $n_D^{16.1}$ 1.4950 |
| 59 | " | " | CH₃ | " | " | " | " | " | " | $n_D^{12.6}$ 1.4906 |
| 60 | H | " | CH₂OCH₃ | " | " | " | " | " | " | $n_D^{20.0}$ 1.4946 |
| 61 | " | " | CH₂SC₂H₅ | " | " | " | " | " | " | $n_D^{12.5}$ 1.5117 |
| 62 | " | " | 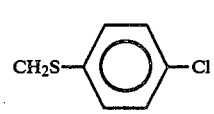 | " | " | " | " | " | " | $n_D^{20.6}$ 1.5630 |
| 63 | " | " | CH₂SCH₃ | " | " | " | " | " | " | $n_D^{27.0}$ 1.5134 |
| 64 | " | " | CH₂OCH₃ | " | S | " | " | " | " | $n_D^{30.2}$ 1.4851 |
| 65 | CH₂SCH₃ | CH₃ | H | " | O | " | " | " | " | $n_D^{28.0}$ 1.5062 |
| 66a | " | H | " | " | " | " | " | " | " | $n_D^{27.4}$ 1.5068 |
| 66b | " | " | " | " | " | " | " | " | " | $n_D^{27.4}$ 1.5102 |
| 67 | COOC₂H₅ | " | " | " | S | S | " | " | " | $n_D^{28.8}$ 1.5408 |
| 68 | C₂H₅ | " | " | " | O | O | S | " | " | $n_D^{28.0}$ 1.5223 |
| 69 | H | " | " | " | " | " | " | " | " | $n_D^{28.3}$ 1.5325 |
| 70 | CH₃ | " | 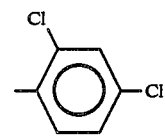 | " | S | " | O | " | " | $n_D^{32.0}$ 1.5539 |
| 71 | H | " | C₃H₇(i) | " | " | S | " | " | " | $n_D^{33.6}$ 1.5505 |
| 72 | CH₃ | " | H | " | O | O | " | C₃H₇(n) | " | $n_D^{25.2}$ 1.4926 |
| 73 | H | " | " | " | " | " | " | " | " | $n_D^{24.6}$ 1.4964 |

TABLE 1-continued $$\begin{array}{c} X_1 \\ X_2 \\ X_3 \\ X_4 \end{array} \bigg\rangle N - P \bigg\langle \begin{array}{c} Z \\ \| \\ Y_1 \end{array} \begin{array}{c} SR_1 \\ OR_2 \end{array} \tag{I}$$

| Compound No. | General formula I | | | | | | | | | Physical property (Refractive index) |
|---|---|---|---|---|---|---|---|---|---|---|
| | $X_1$ | $X_2$ | $X_3$ | $X_4$ | $Y_1$ | $Y_2$ | $Z$ | $R_1$ | $R_2$ | |
| 74 | " | " | CH$_3$ | " | " | " | " | " | " | $n_D^{24.2}$ 1.4916 |

Note:
In Table 1, compounds having the same number with different symbols "a" and "b", "a-I" and "b-I" or "b-II", or "a-II" and "b-I" or "b-II", are diastereomers to each other. Likewise, compounds having the same number with different symbols "a-I" and "a-II", or "b-I" and "b-II" are optical isomers to each other.
(n)—normal
(s)—secondary
(i)—iso
(t)—tertiary The compounds of the present invention show excellent activities as active ingredients for insecticides, miticides and nematocides. For instance, they are effective against plant parasitic mites such as two-spotted spider mite (*Tetranychus urticae*), carmine spider mite (*Tetranychus cinnabarinus*) or citrus red mite (*Panonychus citri*); agricultural insect pests such as diamondback moth (*Plutella xylostella*), cabbage armyworm (*Mamestra brassicae*), common cutworm (*Spodoptera litura*), colorado potato beetle (*Leptinotarsa decemlineata*), codling moth (*Laspeyresia pomonella*), bollworm (*Heliothis zea*), tobacco budworm (*Heliothis virescens*), boll weevil (*Anthonomus grandis*), gypsy moth (*Lymantria dispar*), aphids, planthoppers, leafhoppers, scales, bugs, whiteflies, thrips, grasshoppers anthomyiid flies, scarabs, black cutworm (*Agrotis ipsilon*) or cutworm (*Agrotis segetum*); hygienic insect pests such as tropical rat mite (*Ornithonyssus bacoti*), cockroaches, housefly (*Musca domestica*) or house mosquito (*Culex pipiens pallens*); stored grain insect pests such as azuki bean weevil (*Callosobruchus chinensis*) or confused flour beetle (*Tribolium confusum*); household goods insect pests such as casemaking clothes moth (*Tinea pellionella*), black carpet beetle (*Anthrenus scrophularidae*) or subterranean termites; and other parasites on domestic animals such as fleas, lice or flies. Further, they are also effective against plant parastic nematodes such as root-knot nematodes, cyst nematodes, root-lesion nematodes, rice white-tip nematode (*Aphelenchoides besseyi*), Strawberry bud nematode (*Nothotylenchus acris*) or pine wood nematode (*Bursaphelenchus liqnicolus*). Furthermore, they are effective also against mites having the resistance to dicofol and organophosphorus insecticides and against insect pests such as aphids and housefly having the resistance to organophosphorus insecticides. Moreover, the compounds of the present invention have excellent systemic properties, and by the application of the compounds of the present invention to soil treatment, not only soil insect pests and nematodes but also foliage insect pests can be controlled.

When used as active ingredients for insecticides, miticides or nematicides, the compounds of the present invention may be formulated together with agricultural adjuvants into various forms such as dusts, granules, wettable powders, emulsifiable concentrates, dispersions, aerosols or pastes, just like conventional agricultural chemicals. When such formulations are to be actually used, they may be used as they are or after being diluted with suitable diluents such as water to a predetermined concentration.

Such formulations are usually composed of 0.5-90 parts by weight of active ingredient and 10-99.5 parts by weight of agricultural adjuvants.

As the agricultural adjuvants, there may be mentioned carriers, emulsifiers, suspending agents, dispersants, extenders, penetrating agents, wetting agents, thickeners or stabilizers. They may be added as the case requires. The carriers may be divided into solid carriers and liquid carriers. As the solid carriers, there may be mentioned powders of animal and plant origin, such as starch, activated carbon, soybean flour, wheat flour, wood powder, fish powder or powdered milk; or mineral powders such as talc, kaolin, bentonite, calcium carbonate, zeolite, diatomaceous earth, white carbon, clay, alumina or sulfur powder. As the liquid carriers, there may be mentioned water; alcohols such as methyl alcohol or ethylene glycol; ketones such as acetone or methyl ethyl ketone; ethers such as dioxane or tetrahydrofuran; aliphatic hydrocarbons such as kerosine or the like; aromatic hydrocarbons such as xylene, trimethylbenzene, tetramethylbenzene or solvent naphtha; halogenated hydrocarbons such as chloroform or chlorobenzene; acid amides such as dimethylformamide; esters such as ethyl acetate or glycerine ester of a fatty acid; nitriles such as acetonitrile; or sulfur-containing compounds such as dimethyl sulfoxide.

Further, the compounds of the present invention may be used in combination with other agricultural chemicals such as insecticides, miticides, nematicides, bactericides, antiviral agents, attractants, herbicides or plant growth regulators, as the case requires. In some cases, the effectiveness will be improved by such combination.

For instance, as such insecticides, miticides or nematicides, there may be mentioned organophosphorus compounds such as O-(4-bromo-2-chlorophenyl) O-ethyl S-propyl phosphorothioate, 2,2-dichlorovinyl dimethyl phosphate, ethyl 3-methyl-4-(methylthio)phenyl isopropylphosphoramidate, O,O-dimethyl O-(4-nitro-m-tolyl phosphorothioate, O-ethyl O-(4-nitrophenyl) phenylphosphonothioate, O,O-diethyl O-2-isopropyl-6-methylpyrimidin-4-yl phosphorothioate, O,O-dimethyl O-(3,5,6-trichloro-2-pyridyl) phosphorothioate, O,S-dimethyl acetylphosphoramidothioate or O-(2,4-dichlorophenyl) O-ethyl S-propyl phosphorodithioate; carbamate compounds such as 1-naphthyl methylcarbamate, 2-isopropoxyphenyl methylcarbamate, 2-methyl-2-(methylthio)propionaldehyde O-methylcarbamoyloxime, 2,3-dihydro-2,2-dimethylbenzofuran-7-yl methylcarbamate, bis[N-{1-(methylthio)-ethylideneaminooxycarbonyl}-N-methylamino]sulfide S-methyl N-(methylcarbamoyloxy) thioacetimidate, N,N-dimethyl-2-methylcarbamoyloxyimino-2-(methylthio)acetamide, 2-(ethylthiomethyl)phenyl methylcarbamate 2-dimethylamino-5,6-dimethylpyrimidin-4-yl dimethylcarbamate or S,S'-2-dimethyl aminotrimethylene bis(thiocarbamate); organic chlorine compounds such as 2,2,2-trichloro-1,1-bis(4-chlorophenyl)ethanol or 4-chlorophenyl-2,4,5-trichlorophenyl sulfone; organic metal compounds such as tricyclohexyltin hydroxide; pyrethroide compounds such as (RS)-α-cyano-3-phenoxybenzyl (RS)-2-(4-chlorophenyl)-3-methylbutyrate, 3-phenoxybenzyl (1RS)-cis,trans-3-( 2,2-dichlorovinyl)-2,2-dimethylcyclopropanecarboxylate, (RS)-α-cyano-3-phenoxybenzyl (1RS)-cis,trans-3-(2,2-dichlorovinyl)-2,2-dimethylcyclopropanecarboxylate, (S)-α-cyano-3-phenoxybenzyl (1R)-cis-3-(2,2-dibromovinyl)-2,2-dimethylcyclopropanecarboxylate or (RS)-α-cyano-3-phenoxybenzyl (1RS)-cis-3-(2-chloro-3,3,3-trifluoropropenyl)-2,2-dimethylcyclopropanecarboxylate; benzoyl urea compounds such as 1-(4-chlorophenyl)-3-(2,6-difluorobenzoyl)urea, 1-{3,5-dichloro-4-(3-chloro-5-trifluoromethyl-2-pyridyloxy)-phenyl}-3-(2,6-difluorobenzoyl)urea or 1-(3,5-dichloro-2,4-difluorophenyl)-3-(2,6-difluorobenzoyl)urea; other compounds such as 2-tert-butylimino-3-isopropyl-5-phenyl-3,4,5,6-tetrahydro-2H-1,3,5,-thiadiazin-4-one, 4-methyl-5-(4-chlorophenyl)-3-cyclohexylcarbamoyl-2-thiazo lidone or N-methylbis(2,4-xylyliminomethyl)amine; juvenile hormono-like compounds such as isopropyl-(2E,4E)-11-methoxy-3,7,11-trimethyl-2,4-dodecadienoate; and other compounds such as dinitro compounds, organic sulfur compounds, urea compounds or triazine compounds. Further, microbial insecticide such as *Bacillus thurigiensis* agent or nuclear polyhedrosis virus may also be used in combination with the compounds of the present invention.

As the fungicides, there may be mentioned organophosphorus compounds such as S-benzyl O,O-di-isopropyl phosphorothioate, O-ethyl S,S-diphenyl phosphorodithioate or aluminium ethyl hydrogen phosphonate; organic chlorine compounds such as 4,5,6,7-tetrachlorophthalide or tetrachloroisophthalonitrile; dithiocarbamate compounds such as manganese ethylenebis(dithiocarbamate), zinc ethylenebis(dithiocarbamate), manganese ethylenebis(dithiocarbamate) complex with zinc salt, dizing bis(dimethyldithiocarbamate)-ethylenebis-(dithiocarbamate) or polymeric zinc propylenebis-(dithiocarbamate); N-halogenothioalkyl compounds such as N-(trichloromethylthio)cyclohex-4-ene-1,2-dicarboxymide, N-(1,1,2,2-tetrachloroethylthio)-cyclohex-4-ene-1,2-dicarboximide or N-(trichloromethylthio)phthalimide; dicarboxy imide compounds such as 3-(3,5-dichlorophenyl)-N-isopropyl-2,4-dioxoimidazolidine-1-carboxamide, (RS)-3-(3,5-dichlorophenyl)-5-methyl-5-vinyl-1,3-oxazolidine-2,4-dione or N-(3,5-dichlorophenyl)-1,2-dimethylcyclopropane-1,2-dicarboximide; benzimidazole compounds such as methyl 1-(butylcarbamoyl)-2-benzimidazolecarbamate or dimetyl 4,4'-(o-phenylene)bis(3-thioallophanate); azole compounds such as 1-(4-chlorophenoxy)-3,3-dimethyl-1-(1H-1,2,4-triazol-1-yl)butanone, 1-(biphenyl-4-yloxy)-3,3-dimethyl-1-(1H-1,2,4-triazol-1-yl) butan-2-ol, 1-[N-(4-chloro-2-trifluoromethylphenyl)-2-propoxy-acetimidoyl]imidazole, (±)-1-[2-(2,4-dichlorophenyl)-4-ethyl-1, 3-dioxolan-2-ylmethyl]-1H-1,2,4-triazole, (±)-1-[2-(2,4-dichlorophenyl)-4-propyl-1,3-dioxolan-2-ylmethyl]-1H-1,2,4-triazole or 1-[2-(2,4-dichlorophenyl)pentyl]-1H-1,2,4-triazole; carbinol compounds such as (±)-2,4'-dichloro-α-(pyrimidin-5-yl)benzhydryl alcohol or (±)-2,4'-difluoro-α-(1H-1,2,4-triazol-1-ylmethyl)benzhydryl alcohol; benzanilide compounds such as 3'-isopropoxy-2-methylbenzanilide or 3'-isopropoxy-α,α,α-trifluoro-o-toluanilide; 2,6-dimethyl-N-acylanilide compounds such as methyl N-(2-methoxyacetyl)-N-(2,6-xylyl)-DL-alaninate; and other compounds such as piperazine compounds, morpholine compounds, anthraquinone compounds, quinoxaline compounds, crotonic acid compounds, sulfenic acid compounds, urea compounds or antibiotic substances.

The insecticides, miticides and nematicides of the present invention are effective for the control of various noxious insects, noxious mites and noxious nematodes. They are applied in an active ingredient concentration of from 1 to 20,000 ppm, preferably from 20 to 2,000 ppm. The active ingredient concentration may be optionally changed depending upon the particular formulation, the manner, purpose, timing or place of the application and the condition of the insect pests. For instance, aquatic noxious insects can be controlled by applying the formulation having the above-mentioned concentration to the site of the outbreak, and thus, the concentration of the active ingredient in water is less than the above-mentioned range.

The amount of the application of the active ingredient per unit surface area is usually from about 0.1 to 5,000 g, preferably from 10 to 1,000 g, per 10a. However, in a certain special case, the amount of the application may be outside the above range.

Various formulations containing the compounds of the present invention or their diluted compositions may be applied by conventional methods for application which are commonly employed, such as spraying (e.g. spraying, jetting, misting, atomizing, powder or grain scattering or dispersing in water), soil application (e.g. mixing or drenching), surface application (e.g. coating, powdering or covering) or impregnation to obtain poisonous feed. Further, it is possible to feed domestic animals with a feed containing the above active ingredient and to control the outbreak or growth of pests, particularly insect pests, with their excrements. Furthermore, the active ingredient may also be applied by a so-called ultra low-volume application method. In this method, the composition may be composed of 100% of the active ingredient.

TEST EXAMPLE 1

Each of formulations containing the active ingredients identified in Table 2 was dispersed in water to obtain dispersions of each active ingredient having concentrations of 800 ppm and 200 ppm. Each of French bean seedlings with only one primary leaf left, was transplanted to a cup having a diameter of 7 cm and a height of 4 cm. About 30 nimphs and adults of two-spotted spider mite (*Tetranychus urticae*) were infested to the leaf of the French bean. Then, the French bean was dipped in the dispersion having the above-mentioned predetermined concentration for about 10 seconds, then dried in air and kept in a constant temperature chamber with lightening at 28° C. (in the cases of Compound Nos. 1 to 38) or 26° C. (in other cases). At two days after the treatment, dead mites were counted, and the mortality was calculated by the following equation:

$$\text{Mortality (\%)} = \frac{\text{Number of dead mites}}{\text{Number of total mites}} \times 100$$

The results are shown in Table 2.

TABLE 2

| Compound No. | Mortality (%) 800 ppm of active ingredient | 200 ppm of active ingredient |
|---|---|---|
| 1 | 100 | 100 |
| 2 | 100 | 100 |
| 3 | 100 | 100 |
| 4 | 100 | 100 |
| 5 | 100 | 100 |
| 6 | 100 | 100 |
| 7a | 100 | 100 |
| 7b | 100 | 100 |
| 8a | 100 | 100 |
| 8b | 100 | 100 |
| 9 | 100 | 100 |
| 10 | 100 | 100 |
| 11 | 100 | 100 |
| 12 | 100 | 100 |
| 13 | 100 | 100 |
| 14 | 100 | 100 |
| 15 | 100 | 100 |
| 16 | 100 | 100 |
| 17 | 100 | 100 |
| 18 | 100 | 100 |
| 19 | 100 | — |
| 20 | 100 | 100 |
| 20a | 100 | 100 |
| 20b | 100 | 100 |
| 20a-I | 100 | 100 |
| 20b-I | 100 | 100 |
| 20a-II | 100 | 100 |
| 20b-II | 100 | 100 |
| 21 | 100 | 100 |
| 22a | 100 | 100 |
| 22b | 100 | 100 |
| 23 | 100 | 100 |
| 24 | 100 | 100 |
| 25 | 100 | 100 |
| 26 | 100 | 100 |
| 27a | 100 | 100 |
| 27b | 100 | 100 |
| 28 | 100 | 100 |
| 29 | 100 | 100 |
| 30 | 100 | 100 |
| 31 | 100 | 100 |
| 32 | 100 | 100 |
| 33 | 100 | 100 |
| 34 | 100 | 100 |
| 35 | 100 | 100 |
| 36 | 100 | 100 |
| 37 | 100 | 100 |
| 38 | 100 | 100 |
| 39 | 100 | 100 |
| 40 | 100 | 100 |
| 41 | 100 | 100 |
| 42 | 100 | 100 |
| 43 | 100 | 100 |
| 44 | 100 | 100 |
| 45 | 100 | 100 |
| 46 | 100 | 100 |
| 47 | 100 | 100 |
| 48 | 100 | 100 |
| 49 | 100 | 100 |
| 50 | 100 | 100 |
| 51 | 100 | 100 |
| 52 | 100 | 100 |
| 53 | 100 | 100 |
| 54 | 100 | 100 |
| 55 | 100 | 100 |
| 56a | 100 | 100 |
| 56b | 100 | 100 |
| 57 | 100 | 100 |
| 58 | 100 | 100 |
| 59 | 100 | 100 |
| 60 | 100 | 100 |
| 61 | 100 | 100 |
| 62 | 100 | 100 |
| 63 | 100 | 100 |
| 64 | 100 | 100 |
| 65 | 100 | 100 |
| 66a | 100 | 100 |
| 66b | 100 | 100 |
| 67 | 100 | 100 |
| 68 | 100 | — |
| 69 | 100 | — |
| 70 | 100 | 100 |
| 71 | 100 | 100 |
| 72 | 100 | 100 |
| 73 | 100 | 100 |
| 74 | 100 | 100 |
| Comparative compound* | 40 | 0 |

Note:
*This compound is O,O—diethyl(4,4-dimethyl-2-thiono-3-oxazolidynyl)phosphonate disclosed in Japanese Unexamined Patent Publication No. 144,794/1984.

TEST EXAMPLE 2

Each of formulations containing the active ingredients identified in Table 3, was dispersed in water to obtain dispersions of each active ingredient having concentrations of 800 ppm and 200 ppm. Leaves of cabbage were dipped in the respective dispersions for about 10 seconds, and then dried in air. A sheet of moistened filter paper was placed in a Petri dish having a diameter of 9 cm, and the dried leaves of cabbage were put on the filter paper. Larvae of diamondback moth (*Plutella xylostella*) in second or third instar were released on the leaves, and the Petri dishes were covered and kept in a constant temperature chamber with lightening at a temperature of 26° C. At two days after released, dead insects were counted, and the mortality was calculated by the following equation:

$$\text{Mortality (\%)} = \frac{\text{Number of dead insects}}{\text{Number of total insects}} \times 100$$

The results are shown in Table 3.

TABLE 3

| Compound No. | Mortality (%) 800 ppm of active ingredient | 200 ppm of active ingredient |
|---|---|---|
| 1 | 100 | 100 |
| 2 | 100 | 100 |
| 3 | 100 | 100 |
| 4 | 100 | 100 |
| 5 | 100 | 100 |
| 6 | 100 | 100 |
| 7a | 100 | 100 |
| 7b | 100 | 100 |
| 8a | 100 | 100 |
| 8b | 100 | 100 |
| 9 | 100 | 100 |
| 10 | 100 | 100 |
| 11 | 100 | 100 |
| 12 | 100 | 100 |
| 13 | 100 | 100 |
| 14 | 100 | 90 |
| 15 | 100 | 100 |
| 16 | 100 | 100 |
| 17 | 100 | 90 |
| 18 | 100 | 100 |
| 20 | 100 | 100 |
| 20a | 100 | 100 |
| 20b | 100 | 100 |
| 20a-I | 100 | 100 |
| 20b-I | 100 | 100 |

TABLE 3-continued

| Compound No. | Mortality (%) 800 ppm of active ingredient | 200 ppm of active ingredient |
|---|---|---|
| 20a-II | 100 | — |
| 20b-II | 100 | 100 |
| 21 | 100 | 100 |
| 22a | 100 | 100 |
| 22b | 100 | 100 |
| 23 | 100 | 100 |
| 24 | 100 | 100 |
| 25 | 100 | 100 |
| 26 | 100 | 100 |
| 27a | 100 | 100 |
| 27b | 100 | 100 |
| 28 | 100 | 100 |
| 29 | 100 | 100 |
| 30 | 100 | 100 |
| 31 | 100 | 100 |
| 32 | 100 | 100 |
| 33 | 100 | 100 |
| 34 | 100 | 100 |
| 35 | 100 | 100 |
| 36 | 100 | 100 |
| 37 | 100 | 100 |
| 38 | 100 | 100 |
| 39 | 100 | 100 |
| 40 | 100 | 100 |
| 41 | 100 | 100 |
| 42 | 100 | 100 |
| 43 | 100 | 100 |
| 44 | 100 | 100 |
| 45 | 100 | 100 |
| 46 | 100 | 100 |
| 47 | 100 | 90 |
| 48 | 100 | 100 |
| 49 | 100 | 100 |
| 50 | 100 | 100 |
| 51 | 100 | 100 |
| 52 | 100 | 100 |
| 53 | 100 | 100 |
| 54 | 100 | 100 |
| 55 | 100 | 100 |
| 56a | 100 | 100 |
| 56b | 100 | 100 |
| 57 | 100 | 100 |
| 58 | 100 | 100 |
| 59 | 100 | 100 |
| 60 | 100 | 100 |
| 61 | 100 | 100 |
| 62 | 100 | 100 |
| 63 | 100 | 100 |
| 64 | 100 | 100 |
| 65 | 100 | 100 |
| 66a | 100 | 100 |
| 66b | 100 | 100 |
| 67 | 100 | 100 |
| 68 | 100 | 100 |
| 69 | 100 | 100 |
| 71 | 100 | 100 |
| Comparative Compound* | 0 | 0 |

Note:
*This compound is the same as the comparative compound in table 2.

TEST EXAMPLE 3

The tests were conducted in the same manner as in Test Example 2 except that larvae of common cutworm (*Spodoptera litura*) in second or third instar were used instead of larvae of the diamondback moth in second or third instar. The results are shown in Table 4.

TABLE 4

| Compound No. | Mortality (%) 800 ppm of active ingredient | 200 ppm of active ingredient |
|---|---|---|
| 1 | 100 | 100 |
| 2 | 100 | 100 |
| 3 | 100 | 100 |
| 4 | 100 | 90 |
| 5 | 100 | 100 |
| 6 | 100 | 100 |
| 7a | 100 | 100 |
| 7b | 100 | 100 |
| 8a | 100 | 100 |
| 8b | 100 | 100 |
| 9 | 100 | 100 |
| 10 | 100 | 100 |
| 11 | 100 | 100 |
| 12 | 100 | 100 |
| 13 | 100 | 100 |
| 14 | 100 | 95 |
| 15 | 100 | 100 |
| 16 | 100 | 95 |
| 17 | 100 | 100 |
| 18 | 100 | 100 |
| 20 | 100 | 100 |
| 20a | 100 | 100 |
| 20b | 100 | 100 |
| 20a-I | 100 | 100 |
| 20b-I | 100 | 100 |
| 20a-II | 100 | 90 |
| 20b-II | 100 | 100 |
| 21 | 100 | 100 |
| 22a | 100 | 90 |
| 22b | 100 | 90 |
| 23 | 100 | 95 |
| 24 | 100 | 95 |
| 25 | 100 | 100 |
| 26 | 100 | 100 |
| 27a | 100 | 100 |
| 27b | 100 | 100 |
| 28 | 100 | 100 |
| 29 | 100 | 90 |
| 30 | 100 | 100 |
| 31 | 100 | 100 |
| 32 | 100 | 100 |
| 33 | 100 | 100 |
| 34 | 100 | 100 |
| 35 | 100 | 100 |
| 36 | 100 | 100 |
| 37 | 100 | 100 |
| 38 | 100 | 100 |
| 39 | 100 | 100 |
| 40 | 100 | 90 |
| 41 | 100 | 100 |
| 42 | 100 | — |
| 43 | 100 | — |
| 44 | 100 | 100 |
| 45 | 100 | 100 |
| 46 | 100 | 100 |
| 47 | 100 | 100 |
| 48 | 100 | 90 |
| 49 | 100 | 100 |
| 50 | 100 | — |
| 51 | 100 | — |
| 52 | 100 | 100 |
| 53 | 100 | 100 |
| 54 | 100 | — |
| 55 | 100 | 100 |
| 56a | 100 | 100 |
| 56b | 100 | 100 |
| 57 | 100 | 100 |
| 62 | 100 | 100 |
| 63 | 100 | 100 |
| 64 | 100 | 100 |
| 70 | 100 | 100 |
| 71 | 100 | 100 |
| 72 | 100 | 100 |
| 73 | 100 | 100 |
| 74 | 100 | 100 |
| Comparative compound* | 0 | 0 |

Note:
*This compound is the same as the comparative compound in Table 2.

TEST EXAMPLE 4

Each of French bean seedlings with only one primary leaf left, was transplanted to a cup (same as Test Example 1). Adults of two-spotted spider mite (*Tetranychus urticae*) were infested to the leaf of the French bean and permitted to lay eggs, and then the adults were removed. Then, the French bean was immersed for about 10 seconds in a dispersion prepared by dispersing each of formulations containing the active ingredients identified in Table 5, in water to obtain a predetermined concentration of the active ingredient. Then, the French bean was dried in air, and kept in a constant temperature chamber with lightening at 28° C. (in the cases of Compound Nos. 1 to 37) or 26° C. (in other cases). At five days after the treatment, the hatching of eggs was examined, and the dead egg rate was calculated by the following equation:

$$\text{Dead egg rate (\%)} = \frac{\text{Number of dead eggs}}{\text{Number of total eggs}} \times 100$$

The results are shown in Table 5. Moreover, the number of dead nimphs which had just hatched was regarded as the number of dead eggs.

TABLE 5

| Compound No. | Dead egg rate (%) 800 ppm of active ingredient | 200 ppm of active ingredient |
|---|---|---|
| 1 | 100 | 100 |
| 3 | 100 | 100 |
| 4 | 100 | 100 |
| 5 | 100 | 100 |
| 12 | 100 | 100 |
| 16 | 100 | 100 |
| 17 | 100 | 100 |
| 20 | 100 | 100 |
| 20a | 100 | 100 |
| 20b | 100 | 100 |
| 23 | 100 | 100 |
| 25 | 100 | 100 |
| 37 | 100 | 100 |
| 39 | 100 | 100 |
| 40 | 100 | 100 |
| 58 | 100 | — |
| 61 | 100 | — |
| 62 | 100 | — |
| 70 | 100 | 100 |
| 72 | 100 | 100 |
| 73 | 100 | 100 |
| Comparative compound* | 0 | 0 |

Note:
*This compound is the same as the comparative compound in Table 2.

TEST EXAMPLE 5

A rice seedling was dipped in a dispersion containing 800 ppm of each active ingredient for 10 seconds, then dried in air and put into a test tube with the root portion enclosed by absorbent cotton. Then, 10 adults of small brown planthopper (*Laodelphax striatellus*) were released in the test tube, and the mouth of the test tube was covered with a gauze. Then, the test tube was kept in a constant temperature chamber with lightening at 26° C. At two days after the release, dead insects were counted, and the mortality was calculated in the same manner as in Test Example 2. The results are shown in Table 6.

TABLE 6

| Compound No. | Mortality (%) 800 ppm of active ingredient |
|---|---|
| 1 | 100 |
| 2 | 100 |
| 3 | 100 |
| 4 | 100 |
| 5 | 100 |
| 6 | 100 |
| 7a | 100 |
| 7b | 100 |
| 8a | 100 |
| 8b | 100 |
| 9 | 100 |
| 11 | 100 |
| 12 | 100 |
| 16 | 100 |
| 17 | 100 |
| 20a | 100 |
| 20a-I | 100 |
| 21 | 100 |
| 22a | 100 |
| 22b | 100 |
| 25 | 100 |
| 27a | 100 |
| 28 | 100 |
| 29 | 100 |
| 30 | 100 |
| 31 | 100 |
| 32 | 100 |
| 33 | 100 |
| 34 | 100 |
| 35 | 100 |
| 36 | 100 |
| 37 | 100 |
| 38 | 100 |
| 39 | 100 |
| 40 | 100 |
| 41 | 100 |
| 42 | 100 |
| 43 | 100 |
| 44 | 100 |
| 45 | 100 |
| 46 | 100 |
| 47 | 100 |
| 48 | 100 |
| 49 | 100 |
| 51 | 100 |
| 52 | 100 |
| 53 | 100 |
| 55 | 100 |
| 56a | 100 |
| 56b | 100 |
| 57 | 100 |
| 60 | 100 |
| 61 | 100 |
| 63 | 100 |
| 64 | 100 |
| 65 | 100 |
| 66a | 100 |
| 66b | 100 |
| 68 | 100 |
| 69 | 100 |
| 72 | 100 |
| 73 | 100 |
| Comparative compound* | 30 |

Note:
*This compound is the same as the comparative compound in Table 2.

TEST EXAMPLE 6

The soil contaminated by southern root-knot nematode (*Meloidgyne incognita*) was put in a pot of 1/5,000a., and a dispersion containing an active ingredient was pourded into the pot to bring the concentration of the active ingredient to 250 g/a. At two days after the treatment, the treated soil was mixed, and a tomato seedling in 3-or 4-leaf stage was transplanted in the pot.

At twenty days after the treatment of the active ingredient, the root-gall index was investigated. The results are shown in Table 7. The root-gall index was determined based on the following standards:

0: No galls
1: 1–25% of roots galled
2: 26–50% of roots galled
3: 51–75% of roots galled
4: 76–100% of roots galled

TABLE 7

| Compound No. | Root-gall index |
|---|---|
| 1 | 0 |
| 2 | 0 |
| 3 | 0 |
| 4 | 0 |
| 5 | 0 |
| 6 | 1 |
| 7a | 0 |
| 7b | 0 |
| 8a | 0 |
| 8b | 0 |
| 9 | 0 |
| 10 | 0 |
| 11 | 2 |
| 12 | 0 |
| 13 | 1 |
| 14 | 1 |
| 15 | 0 |
| 16 | 1 |
| 17 | 1 |
| 18 | 0 |
| 20 | 0 |
| 20a | 0 |
| 20b | 0 |
| 20a-I | 0 |
| 20b-I | 0 |
| 20a-II | 1 |
| 20b-II | 0 |
| 21 | 0 |
| 22a | 0 |
| 22b | 0 |
| 23 | 0 |
| 24 | 0 |
| 25 | 0 |
| 26 | 0 |
| 27a | 0 |
| 27b | 0 |
| 28 | 0 |
| 29 | 0 |
| 30 | 0 |
| 31 | 0 |
| 32 | 0 |
| 33 | 0 |
| 34 | 0 |
| 35 | 0 |
| 36 | 0 |
| 37 | 0 |
| 38 | 0 |
| 39 | 0 |
| 40 | 0 |
| 41 | 0 |
| 42 | 0 |
| 43 | 0 |
| 44 | 0 |
| 45 | 0 |
| 46 | 0 |
| 47 | 0 |
| 48 | 0 |
| 49 | 0 |
| 50 | 1 |
| 51 | 0 |
| 52 | 0 |
| 53 | 0 |
| 54 | 0 |
| 55 | 0 |
| 56a | 0 |
| 56b | 0 |
| 57 | 0 |
| 58 | 0 |
| 59 | 0 |
| 60 | 0 |
| 61 | 0 |
| 62 | 1 |
| 63 | 0 |
| 64 | 0 |
| 65 | 0 |
| 66a | 0 |
| 66b | 0 |
| 67 | 0 |
| 68 | 2 |
| 69 | 1 |
| 71 | 1 |

TEST EXAMPLE 7

Each of formulations containing active ingredients, was dispersed in water to obtain a dispersion having a predetermined concentration. Leaves of cabbage were dipped in the dispersion for about 10 seconds, and then dried in air. A sheet of moistened filter paper was placed in a Petri dish having a diameter of 9 cm, and the dried leaves of cabbage were put on the sheet. Apterous viviparous females of green peach aphid (*Myzus persicae*) were released on the leaves, and the Petri dish was covered and kept in a constant temperature chamber with lightening at 26° C. At two days after the release, dead insects were counted, and the mortality was calculated in the same manner as in Test Example 2. The results are shown in Table 8.

TABLE 8

| Compound No. | Mortality (%) 800 ppm of active ingredient | 200 ppm of active ingredient |
|---|---|---|
| 1 | 100 | — |
| 2 | 100 | — |
| 3 | 100 | — |
| 4 | 100 | 100 |
| 5 | 100 | 100 |
| 6 | 100 | 100 |
| 7a | 100 | 100 |
| 7b | 100 | 100 |
| 8a | 100 | 100 |
| 8b | 100 | 100 |
| 9 | 100 | 100 |
| 10 | 100 | 100 |
| 11 | 100 | 100 |
| 12 | 100 | 100 |
| 13 | 100 | 100 |
| 14 | 100 | 100 |
| 15 | 100 | 100 |
| 16 | 100 | 100 |
| 17 | 100 | 100 |
| 18 | 100 | 100 |
| 20a-I | 100 | 100 |
| 20b-I | 100 | 100 |
| 20a-II | 100 | 100 |
| 20b-II | 100 | 100 |
| 21 | 100 | 100 |
| 22a | 100 | 100 |
| 22b | 100 | 100 |
| 23 | 100 | 100 |
| 24 | 100 | 100 |
| 25 | 100 | 100 |
| 26 | 100 | 100 |
| 27a | 100 | 100 |
| 27b | 100 | 100 |
| 28 | 100 | — |
| 29 | 100 | 100 |
| 30 | 100 | 100 |
| 31 | 100 | 100 |

TABLE 8-continued

| Compound No. | Mortality (%) 800 ppm of active ingredient | 200 ppm of active ingredient |
|---|---|---|
| 32 | 100 | 100 |
| 33 | 100 | 100 |
| 34 | 100 | 100 |
| 35 | 100 | 100 |
| 36 | 100 | 100 |
| 37 | 100 | 100 |
| 38 | 100 | 100 |
| 39 | 100 | 100 |
| 40 | 100 | 100 |
| 41 | 100 | 100 |
| 42 | 100 | 100 |
| 43 | 100 | 100 |
| 44 | 100 | 100 |
| 45 | 100 | 100 |
| 46 | 100 | 100 |
| 47 | 100 | 90 |
| 48 | 100 | 100 |
| 49 | 100 | 100 |
| 51 | 100 | — |
| 52 | 100 | 100 |
| 53 | 100 | 100 |
| 54 | 100 | 100 |
| 55 | 100 | 100 |
| 56a | 100 | 100 |
| 56b | 100 | 100 |
| 57 | 100 | — |
| 58 | 100 | 100 |
| 59 | 100 | 100 |
| 60 | 100 | 100 |
| 61 | 100 | 100 |
| 62 | 100 | 100 |
| 63 | 100 | 100 |
| 64 | 100 | 100 |
| 65 | 100 | 100 |
| 66a | 100 | — |
| 66b | 100 | — |
| 68 | 100 | 100 |
| 69 | 100 | 100 |
| 71 | 100 | 100 |
| 72 | 100 | 100 |
| 73 | 100 | 100 |
| 74 | 100 | — |
| Comparative compound* | 0 | 0 |

Note:
*This compound is the same as the comparative compound in Table 2.

TEST EXAMPLE 8

Each of formulations containing the active ingredients identified in Table 9, was dispersed in water to obtain a dispersion having a predetermined concentration. Each of French bean seedlings with only one primary leaf left, was transplanted to a cup (same as the Test Example 1), and about 30 nimphs and adults of two-spotted spider mite (*Tetranychus urticae*) having the resistance to dicofol and organophosphorus insecticides, were infested to the French bean. Then, the French bean was dipped in the dispersion having the above-mentioned predetermined concentration for about 10 seconds, then dried in air and kept in a constant temperature chamber with lightening at a temperature of 28° C. (in the cases of Compound Nos. 1 to 38) or 26° C. (in other cases). At two days after the treatment, the dead mites were counted, and the mortality was calculated in the same manner as in Test Example 1. The results are shown in Table 9.

TABLE 9

| Compound No. | Mortality (%) 100 ppm of active ingredient | 50 ppm of active ingredient |
|---|---|---|
| 1 | 100 | 100 |
| 2 | 100 | 100 |
| 3 | 100 | 100 |
| 4 | 100 | 100 |
| 5 | 100 | 86 |
| 6 | 100 | 90 |
| 7a | 95 | 88 |
| 7b | 100 | 75 |
| 8a | 100 | 96 |
| 9 | 100 | 100 |
| 10 | 85 | 50 |
| 11 | 100 | 80 |
| 12 | 100 | 100 |
| 13 | 100 | 90 |
| 14 | 91 | 93 |
| 15 | 94 | 92 |
| 16 | 100 | 100 |
| 17 | 100 | 100 |
| 18 | 100 | 75 |
| 20a | 100 | 100 |
| 20b | 93 | 94 |
| 20a-I | 100 | 100 |
| 20b-II | 100 | 100 |
| 21 | 100 | 65 |
| 22a | 100 | 36 |
| 23 | 93 | 87 |
| 24 | 100 | 100 |
| 25 | 100 | 100 |
| 26 | 100 | 100 |
| 27a | 100 | 100 |
| 27b | 100 | 93 |
| 28 | 100 | 71 |
| 29 | 100 | 95 |
| 30 | 100 | 90 |
| 31 | 96 | 67 |
| 32 | 100 | 100 |
| 33 | 100 | 100 |
| 34 | 100 | 95 |
| 35 | 100 | 60 |
| 36 | 100 | 100 |
| 37 | 93 | 63 |
| 38 | 100 | 44 |
| 39 | 100 | 80 |
| 41 | 100 | 100 |
| 46 | 100 | 72 |
| 48 | 90 | 74 |
| 51 | 100 | 84 |
| 52 | 93 | 86 |
| 53 | 100 | 75 |
| 54 | 100 | 100 |
| 55 | 100 | 100 |
| 56b | 100 | 90 |
| 57 | 100 | 100 |
| 58 | 100 | 52 |
| 59 | 100 | 77 |
| 61 | 100 | 31 |
| 63 | 100 | 75 |
| 64 | 100 | 19 |
| 65 | 100 | 100 |
| 66a | 88 | 77 |
| 66b | 88 | 75 |
| 67 | 100 | 95 |
| 70 | 100 | 100 |
| 71 | 100 | 100 |
| 72 | 100 | 100 |
| 73 | 100 | 100 |
| 74 | 100 | 100 |
| Dicofol* | 85 | 10 |
| Metasus tox* | 0 | 0 |
| Comparative compound** | 0 | 0 |

Note:
*Comparative Examples
**This compound is the same as comparative compound in Table 2.

TEST EXAMPLE 9

Each of formulations containing the active ingredients identified in Table 10, was dispersed in water to obtain a dispersion containing 100 ppm of the active ingredient. Each of French bean seedlings having two primary leaves, was transplanted to a cup (same as the Test Example 1), and 10 ml of the dispersion having the above-mentioned concentration was applied by soil drenching. At two days after the treatment, about 30 nimphs and adults of two-spotted spider mite (*Tetranychus urticae*) having the resistance to dicofol and organophosphorus insecticides, were infested to the leaves, and the cup was kept in a constant temperature chamber with lightening at 26° C. At two days after infestation, the dead mites were counted, and the mortality was calculated in the same manner as in Test Example 1. The results are shown in Table 10.

TABLE 10

| Compound No. | Mortality rate (%) |
|---|---|
| 4 | 100 |
| 5 | 100 |
| 7a | 92 |
| 7b | 100 |
| 9 | 100 |
| 18 | 100 |
| 20 | 100 |
| 20a | 100 |
| 20b | 100 |
| 20a-I | 100 |
| 20b-I | 100 |
| 20a-II | 100 |
| 20b-II | 100 |
| 22a | 100 |
| 22b | 100 |
| 23 | 100 |
| 24 | 100 |
| 25 | 100 |
| 26 | 100 |
| 27a | 100 |
| 27b | 100 |
| 28 | 100 |
| 29 | 100 |
| 30 | 90 |
| 36 | 100 |
| 37 | 100 |
| 38 | 80 |
| 39 | 100 |
| 41 | 100 |
| 45 | 100 |
| 46 | 100 |
| 49 | 100 |
| 53 | 81 |
| 55 | 100 |
| 60 | 100 |
| 61 | 80 |
| 65 | 95 |
| 66a | 100 |
| 66b | 100 |
| 72 | 100 |
| 73 | 100 |
| 74 | 100 |

TEST EXAMPLE 10

40 g of dried soil was put into an icecream cup, and 10 ml of a dispersion of 500 ppm of an active ingredient, was poured to the soil. The soil was uniformly mixed. Twenty-four hours later, an onion piece as feed was put in the soil, and 10 larvae of onion maggot (*Hylemya untiqua*) of 10 days old were released on the soil. At forty-eight hours after the release, the dead insects were counted, and the mortality was calculated in the same manner as in Test Example 2. The results are shown in Table 11.

TABLE 11

| Compound No. | Mortality rate (%) |
|---|---|
| 1 | 100 |
| 2 | 100 |
| 3 | 100 |
| 4 | 100 |
| 5 | 100 |
| 6 | 100 |
| 7a | 100 |
| 7b | 100 |
| 8a | 100 |
| 8b | 100 |
| 9 | 100 |
| 10 | 100 |
| 11 | 100 |
| 13 | 100 |
| 14 | 100 |
| 15 | 100 |
| 17 | 100 |
| 20b | 100 |
| 20a-I | 100 |
| 20b-II | 100 |
| 22a | 100 |
| 22b | 100 |
| 25 | 100 |
| 26 | 100 |
| 27a | 100 |
| 27b | 100 |
| 29 | 100 |
| 39 | 100 |
| 41 | 100 |
| 52 | 100 |
| 55 | 100 |
| 60 | 100 |

TEST EXAMPLE 11

Tests were conducted in the same manner as in Test Example 7 except that green peach aphid (*Myzus persicae*) having the resistance to organophosphorus insecticides was used instead of ordinary green peach aphid. The results are shown in Table 12.

TABLE 12

| Compound No. | Mortality rate (%) 800 ppm of active ingredient |
|---|---|
| 3 | 100 |
| 4 | 100 |
| 5 | 100 |
| 7a | 100 |
| 7b | 100 |
| 8b | 100 |
| 9 | 100 |
| 12 | 100 |
| 20a-I | 100 |
| 20b-II | 100 |
| 21 | 100 |
| 22a | 100 |
| 23 | 100 |
| 26 | 100 |
| 29 | 100 |
| 32 | 100 |
| 33 | 100 |
| 34 | 100 |
| 36 | 100 |
| 37 | 100 |
| 38 | 100 |
| 39 | 100 |
| 41 | 100 |
| 45 | 100 |
| 46 | 100 |
| 48 | 100 |
| 49 | 100 |
| 52 | 100 |
| 54 | 100 |

TABLE 12-continued

| Compound No. | Mortality rate (%) 800 ppm of active ingredient |
|---|---|
| 55 | 100 |
| 56a | 100 |
| 56b | 100 |
| 59 | 100 |
| 60 | 100 |
| 63 | 100 |
| Fenitrothion* | 0 |
| Dimethoate* | 20 |
| Diaginon* | 30 |
| Comparative compound** | 0 |

Note:
*Comparative Examples
**This compound is the same as the comparative compound in Table 2.

TEST EXAMPLE 12

A sheet of filter paper having a diameter of 7 cm was placed in an icecream cup and 1 ml of a dispersion having a concentration of an active ingredient of 800 ppm in water, was dropped onto the filter paper. Twenty houseflies having the resistance to organophosphorus insecticides (No. 3 Yume-no-shima colony) were released in the icecream cup, and the icecream cup was kept in a constant temperature chamber with lightening at 26° C. At one day after the release, the dead flies were counted, and the mortality was calculated in the same manner as in Test Example 2. The results are shown in Table 13.

TABLE 13

| Compound No. | Mortality rate (%) |
|---|---|
| 1 | 100 |
| 4 | 100 |
| 5 | 100 |
| 7a | 100 |
| 8a | 100 |
| 8b | 100 |
| 20 | 100 |
| 20a | 100 |
| 20b | 100 |
| 20a-I | 100 |
| 20b-II | 100 |
| 39 | 100 |
| 41 | 100 |
| Fenitrothion* | 60 |
| Malathion* | 60 |

Note:
*Comparative Examples

Formulation Example 1

(a) Compound No. 1: 20 Parts by weight
(b) N,N'-dimethylformamide: 70 Parts by weight
(c) Polyoxyethylenealkylphenyl ether: 8 Parts by weight The above components are uniformly mixed and dissolved to obtain an emulsifiable concentrate.

Formulation Example 2

(a) Compound No. 41: 50 Parts by weight
(b) Tetramethylbenzene: 38 Parts by weight
(c) An emulsifier mixture comprising an alkylbenzene sulfonate, a polyoxyethylenealkylphenol ether and a polyoxyethylenephenylphenol ether (Aglysol P-311 (Trade name), manufactured by Kao Soap Co. Ltd.): 12 Parts by weight The above components are uniformly mixed and dissolved to obtain an emulsifiable concentrate.

Formulation Example 3

(a) Compound No. 8a: 85 Parts by weight
(b) The emulsifier mixture as used in Formulation Example 2: 15 Parts by weight The above components are uniformly mixed to obtain a highly concentrated emulsifiable concentrate.

Formulation Example 4

(a) Compound No. 63: 5 Parts by weight
(b) Talc: 95 Parts by weight

The above components are uniformly mixed to obtain a dust.

Formulation Example 5

(a) Compound No. 20a: 5 Parts by weight
(b) Bentonite: 45 Parts by weight
(c) Kaoline: 50 Parts by weight The above components are kneaded together with a small amount of water, then extruded in a granular form and dried to obtain granules.

Formulation Example 6

(a) Compound No. 5: 0.50 Part by weight
(b) Polyoxyethyleneoctylphenyl ether: 0.15 Part by weight
(c) Polyoxyethylene phosphate: 0.10 Part by weight
(d) Granular calcium carbonate: 99.25 Parts by weight Components (a) to (c) are preliminarily uniformly mixed, then diluted with a proper amount of acetone, and then sprayed on component (d), and then acetone was removed to obtain granules.

Formulation Example 7

(a) Compound No. 7a: 50 Parts by weight
(b) Fine silica powder: 15 Parts by weight
(c) Fine clay powder: 25 Parts by weight
(d) A condensation product of sodium naphthalenesulfonate sulfonate with formalin: 2 Parts by weight
(e) Dialkyl sulfosuccinate: 3 Parts by weight
(f) Polyoxyethylenealkylallyl ether sulfate: 5 Parts by weight The above components are uniformly pulverized and mixed to obtain a wettable powder.

Formulation Example 8

(a) Compound No. 34: 5 Parts by weight
(b) Glycerin: 5 Parts by weight
(c) Milk powder: 3 Parts by weight
(d) Fish powder: 87 Parts by weight The above components are uniformly kneaded to obtain a paste.

Formulation Example 9

(a) Compound No. 39: 10 Parts by weight
(b) Polyoxyethyleneoctylphenyl ether: 3 Parts by weight
(c) Kerosine: 87 Parts by weight The above components are uniformly mixed and dissolved to obtain an aerosol to be sprayed by compressed air.

We claim:

1. An organophosphorus compound represented by the general formula:

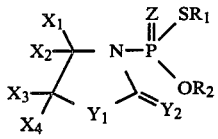 (I)

where each of $X_1$ and $X_3$ is a hydrogen atom; an alkyl or alkoxy group which may be substituted by halogen, alkoxy, alkylthio, phenoxy, halogenated phenoxy, phenylthio or halogenated phenylthio; a carboxyl group; an alkoxycarbonyl group; or a phenyl group which may be substituted by halogen, each of $X_2$ and $X_4$ is a hydrogen atom or an alkyl group, provided that $X_2$ and $X_3$ may together form an alkylene group, each of $Y_1$, $Y_2$ and $Z$ is an oxygen atom or a sulfur atom, and each of $R_1$ and $R_2$ is an alkyl group.

2. The organophosphorus compound of the formula I according to claim 1, wherein Z is an oxygen atom.

3. The organophosphorus compound of the formula I according to claim 1, wherein each of $X_1$ and $X_3$ is a hydrogen atom; a lower alkyl or lower alkoxy group which may be substituted by alkoxy or alkylthio; or a phenyl group which may be substituted by halogen, each of $X_2$ and $X_4$ is a hydrogen atom or a lower alkyl group, Z is an oxygen atom, and each of $R_1$ and $R_2$ is a lower alkyl group.

4. The organophosphorus compound of the formula I according to claim 1, wherein each of $X_1$ and $X_3$ is a hydrogen atom; a lower alkyl group which may be substituted by alkoxy or alkylthio; or a lower alkoxy group, each of $X_2$ and $X_4$ is a hydrogen atom or a lower alkyl group, Z is an oxygen atom, and each of $R_1$ and $R_2$ is a lower alkyl group, provided that $R_1$ and $R_2$ are different from each other.

5. The organophosphorus compound of the formula I according to claim 4, wherein $Y_2$ is an oxygen atom.

6. The organophosphorus compound of the formula I according to claim 1, wherein each of $X_1$ and $X_3$ is a hydrogen atom or a lower alkyl group, each of $X_2$ and $X_4$ is a hydrogen atom or a lower alkyl group, each of $Y_2$ and Z is an oxygen atom, and each of $R_1$ and $R_2$ is a lower alkyl group, provided that $R_1$ and $R_2$ are different from each other.

7. The organophosphorus compound of the formula I according to claim 1, wherein each of $X_1$ and $X_3$ is a hydrogen atom or a lower alkyl group, each of $X_2$ and $X_4$ is a hydrogen atom or a lower alkyl group, each of $Y_2$ and Z is an oxygen atom, $R_1$ is a n-propyl group, an iso-butyl group or a sec-butyl group, and $R_2$ is a methyl group or an ethyl group.

8. The organophosphorus compound of the formula I according to claim 1, wherein each of $X_1$ and $X_3$ is a hydrogen atom or a lower alkyl group, each of $X_2$ and $X_4$ is a hydrogen atom, each of $Y_2$ and Z is an oxygen atom, $R_1$ is a n-propyl group, an iso-butyl group or a sec-butyl group, and $R_2$ is a methyl group or an ethyl group.

9. S-sec-butyl O-ethyl (2-oxo-3-thiazolidinyl)phosphonothiolate according to claim 1.

10. S-sec-butyl O-ethyl (4-methyl-2-oxo-3-oxazolidinyl)-phosphonothiolate according to claim 1.

11. S-sec-butyl O-ethyl (4-ethyl-2-oxo-3-oxazolidinyl)-phosphonothiolate according to claim 1.

12. S-sec-butyl O-ethyl (4,4-dimethyl-2-oxo-3-oxazolidinyl)phosphonothiolate according to claim 1.

13. An insecticidal, miticidal or nematicidal composition comprising an insecticidally, miticidally or nematicidally effective amount of an organophosphorus compound of the formula I as defined in claim 1 and, a carrier.

* * * * *